United States Patent [19]

Hoeltje et al.

[11] Patent Number: 4,987,137
[45] Date of Patent: Jan. 22, 1991

[54] CERTAIN 6,7,8,9-TETRAHYDROPYRIDO[1,2-α]INDOLES AND THEIR USE FOR THE TREATMENT OF CERBROVASCULAR DISORDERS

[75] Inventors: Dagmar Hoeltje, Gronau; Dietrich Thielke, Wallenstedt, both of Fed. Rep. of Germany

[73] Assignee: Beecham Wuelfing GmbH & Co., KG, Fed. Rep. of Germany

[21] Appl. No.: 341,380

[22] Filed: Apr. 20, 1989

Related U.S. Application Data

[62] Division of Ser. No. 879,057, Jun. 26, 1986, Pat. No. 4,835,271.

[30] Foreign Application Priority Data

Jun. 28, 1985 [GB] United Kingdom ............... 8516390
Dec. 23, 1985 [GB] United Kingdom ............... 8531634

[51] Int. Cl.$^5$ ................. C07D 471/02; A61K 31/435
[52] U.S. Cl. ...................................... 514/294; 546/94; 546/200; 540/202; 540/467; 544/126
[58] Field of Search ............................ 546/94; 514/294

[56] References Cited

U.S. PATENT DOCUMENTS

| | | | |
|---|---|---|---|
| 4,328,343 | 5/1982 | Vollhardt et al. | 546/145 |
| 4,595,688 | 1/1986 | Maryanoff | 546/94 |
| 4,624,954 | 11/1986 | Jirkovsky et al. | 514/290 |

FOREIGN PATENT DOCUMENTS

| | | | |
|---|---|---|---|
| 167901 | 1/1986 | European Pat. Off. | 546/94 |
| 1550496 | 8/1979 | United Kingdom | 546/63 |

OTHER PUBLICATIONS

Yoshio et al., J. Am. Chem. Soc. 1981, 103, 6990-2.
Yoshio et al, Chem. Abstracts, vol. 100, 175109c.
Yoshio et al, Chem. Abstracts, vol. 96, 20336z.
Cole, Susan Chem. Abstracts, vol. 92, 198605s.
Verpoorte et al, Chem. Abstracts, vol. 100, 64933x.
Yoshio et al, Chem. Abstracts, vol. 92, 198606t (1980).
Verpoorte et al, J. Med. Plant Res., 48, (1983) 283-289.

*Primary Examiner*—Alan L. Rotman
*Attorney, Agent, or Firm*—Jacobs & Jacobs

[57] ABSTRACT

A compound of formula (I) or a pharmaceutically acceptable salt thereof;

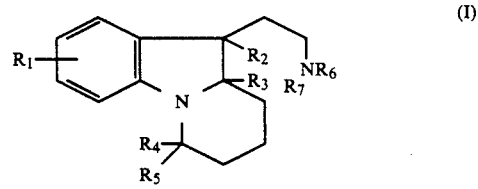

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is $C_{1-7}$ alkyl substituted by $NR_8R_9$ where $R_8$ and $R_9$ are independently hydrogen or $C_{1-4}$ alkyl or together are $C_{3-7}$ polymethylene optionally containing a further heteroatom which is oxygen, sulphur or nitrogen substituted by $R_{10}$ where $R_{10}$ is hydrogen, $C_{1-4}$ alkyl or benzyl, and optionally substituted by one or two $C_{1-4}$ alkyl, $C_{2-5}$ alkanoyl, $C_{1-4}$ alkoxycarbonyl, aminocarbonyl optionally substituted by one or two $C_{1-6}$ alkyl groups or by a benzyl group, cyano, phenyl or benzyl and wherein any phenyl or benzyl group is optionally substituted in the phenyl ring by one or two halo, $CF_3$, $C_{1-4}$ alkyl, $C_{1-4}$ alkoxy, cyano or nitro groups; and $R_7$ is hydrogen or $C_{1-4}$ alkyl.

10 Claims, No Drawings

CERTAIN 6,7,8,9-TETRAHYDROPYRIDO[1,2-a]INDOLES AND THEIR USE FOR THE TREATMENT OF CERBROVASCULAR DISORDERS

CROSS-REFERENCE

This is a division of Ser. No. 879,057 filed June 26, 1986, U.S. Pat. No. 4,835,271.

This invention relates to compounds having pharmacological activity, to a process for their preparation and their use as pharmaceuticals.

J. Am. Chem. Soc. 1981, 103, 6990–6992 discloses secocanthine derivatives of formula (A):

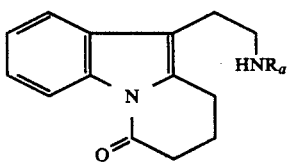

(A)

wherein Ra is hydrogen or benzyl. No pharmacological activity is disclosed for these compounds.

EP-0167901-A published on 15th Jan. 1986, discloses a pharmaceutical composition comprising a compound of formula (B) or a pharmaceutically acceptable salt thereof:

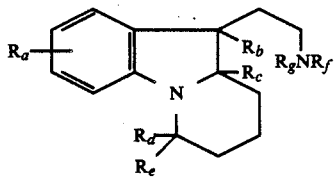

(B)

wherein:

$R_a$ is hydrogen, $C_{1-6}$ alkyl, $C_{1-6}$ alkoxy or halogen;

$R_b$ and $R_c$ are both hydrogen or together represent a bond;

$R_d$ is hydrogen and $R_e$ is hydrogen or $R_d$ and $R_e$ together represent an oxo group;

$R_f$ is hydrogen; $C_{1-6}$ alkyl; $C_{3-7}$ cycloalkyl; $C_{3-7}$ cycloalkyl-$C_{1-4}$ alkyl; phenyl or phenyl $C_{1-7}$ alkyl in which the phenyl moiety is optionally substituted by one or two of halogen, ortho-nitro, meta-or para-methoxy, methyl or $NR_hR_i$ wherein $R_h$ and $R_i$ are independently hydrogen or $C_{1-6}$ alkyl or $R_h$ and $R_i$ together are $C_{2-6}$ polymethylene, or 3,4-disubstituted by methylenedioxy or ethylenedioxy; or monocyclic heteroaryl-$C_{1-4}$ alkyl or aliphatic heterocyclyl-$C_{1-4}$ alkyl of up to six ring atoms, the heteroatom(s) being selected from oxygen, sulphur or nitrogen, any amino nitrogen heteroatom optionally $C_{1-4}$ alkyl substituted; and $R_g$ is hydrogen or $C_{1-4}$ alkyl; and a pharmaceutically acceptable carrier.

It is disclosed that the compounds have anti-hypoxic activity and/or activity against cerebral oxygen deficiency and are therefore useful in treating cerebrovascular disorders and disorders associated with cerebral senility.

A further group of secocanthine derivatives have now been discovered to have anti-ischaemic activity, in particular anti-hypoxic activity and/or activity against cerebral oxygen deficiency.

Accordingly, the present invention provides a compound of formula (I) or a pharmaceutically acceptable salt thereof:

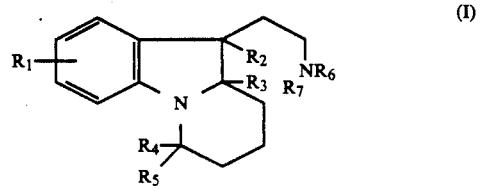

(I)

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is $C_{1-7}$ alkyl substituted by $NR_8R_9$ are independently hydrogen or $C_{1-4}$ alkyl or together are $C_{3-7}$ polymethylene optionally containing a further hetereoatom which is oxygen, sulphur or nitrogen substituted by $R_{10}$ where $R_{10}$ is hydrogen, $C_{1-4}$ alkyl or benzyl, and optionally substituted by one or two $C_{1-4}$ alkyl, $C_{2-5}$ alkanoyl, $C_{1-4}$ alkoxycarbonyl, aminocarbonyl optionally substituted by one or two $C_{1-6}$ alkyl groups or by a benzyl group, cyano, phenyl or benzyl and wherein any phenyl or benzyl group is optionally substituted in the phenyl ring by one or two halo, $CF_3$, $C_{1-4}$ alkyl, $C_{1-4}$ alkoxy, cyano or nitro groups; and $R_7$ is hydrogen or $C_{1-4}$ alkyl.

The compounds of the present invention have anti-ischaemic activity, in particular anti-hypoxic activity and/or activity against cerebral oxygen deficiency and are therefore useful in treating cerebrovascular disorders and disorders associated with cerebral senility.

Suitable examples of $R_1$ include hydrogen, methyl, ethyl, n- and iso - propyl, n-, sec-, iso- and tert-butyl, methoxy, ethoxy, fluoro and chloro. $R_1$ is preferably hydrogen or methyl, most preferably hydrogen.

$R_2$ and $R_3$ preferably together represent a bond. $R_4$ and $R_5$ are preferably both hydrogen.

$R_6$ is preferably $C_{3-7}$ alkyl, such as $C_{4-6}$ or $C_{5-7}$ alkyl, substituted by $NR_8 R_9$ where $R_8$ and $R_9$ are as defined above. Suitable alkylene chain lengths in $R_6$ include $C_3$, $C_4$ and $C_5$.

When $NR_8 R_9$ is a cyclic moiety, it preferably comprises 5 to 7 ring atoms, more preferably 5 or 6 ring atoms.

Suitable examples of cyclic aminoalkyl $R_6$ include $NR_8R_9C_{1-7}$ alkyl where $R_8$ and $R_9$ together form a piperidine, pyrrolidine, piperazine or morpholine ring. Suitable examples of optional substitutes on cyclic amino $C_{1-7}$ alkyl $R_6$ include one or two $C_{1-4}$ alkyl groups such as methyl, ethyl, n- and iso-propyl, and n-, sec-, iso- and t-butyl.

Suitable examples of acyclic amino alkyl $R_6$ include $C_{1-4}$ alkyl amino $C_{1-7}$ alkyl and di-$C_{1-4}$ alkylamino $C_{1-7}$ alkyl, such as methylamino-, ethylamino-, n- or iso-propylamino-, iso-propylamino-, iso-butylamino-, dimethylamino-, diethylamino, di-n- or iso-propylamino-and di-iso-butylamino $C_{1-7}$ alkyl.

Suitable examples of $R_7$ include hydrogen, methyl, ethyl, n- and iso-propyl, n-, sec-, iso- and tert-butyl. $R_7$ is preferably hydrogen.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

There is a favourable group of compounds within formula (I) of formula (II):

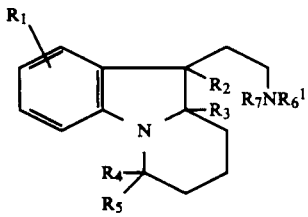
(II)

wherein $R_1$, $R_2$, $R_3$, $R_4$, $R_5$ and $R_7$ are as defined in formula (I) and $R_6^1$ is $NR_8^1 R_9^1 C_{1-7}$ alkyl where $R_8^1$ and $R_9^1$ together are $C_{3-7}$ polymethylene optionally containing a further heteroatom as defined above for $R_8$ and $R_9$ and optionally substituted by one or two $C_{1-4}$ alkyl groups. Suitable and preferred values for $R_1$, $R_2$, $R_3$, $R_4$, $R_5$, $R_6^1$, $R_7$, $R_8^1$ and $R_9^1$ are as described under formula (I) for $R_1$, $R_2$, $R_3$, $R_4$, $R_5$, $R_6$, $R_7$, $R_8$ and $R_9$.

There is a sub-group of compounds within formula (II) of formula (IIa):

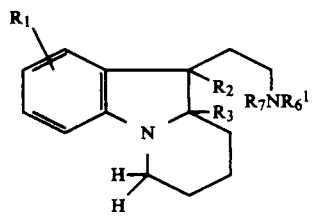
(IIa)

wherein $R_1$, $R_2$, $R_3$, $R_6^1$ and $R_7$ are as defined in formula (II).

Suitable and preferred values for the variables are as described for the corresponding variables under formula (I).

There is a sub-group of compounds within formula (IIa) of formula (IIb):

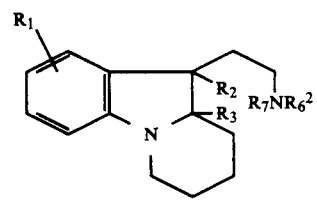
(IIb)

wherein $R_1$, $R_2$, $R_3$ and $R_7$ are as defined in formula (I) and $R_6^2$ is (1-piperidyl)$C_{1-7}$ alkyl substituted by one or two $C_{1-4}$ alkyl groups.

Suitable and preferred values for the variables are as described for the corresponding variables under formula (I).

There is another sub-group of compounds within formula (IIa) of formula (IIc):

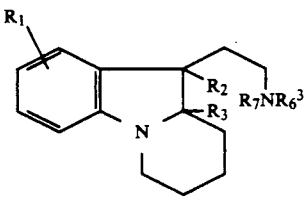
(IIc)

wherein $R_1$, $R_2$, $R_3$, and $R_7$ are as defined in formula (I) and $R_6^3$ is $-(CH_2)_5 NR_8^1 R_9^1$ where $R_8^1$ and $R_9^1$ are as defined in formula (II).

Preferably $R_1$ is hydrogen.
Preferably $R_2$ and $R_3$ represent a bond.
Preferably $R_6^2$ or $R_6^3$ is 5-(3,5-dimethyl-1-piperidyl)pentyl.
Preferably $R_7$ is hydrogen.

There is a further group of compounds within formula (II) of formula (IId):

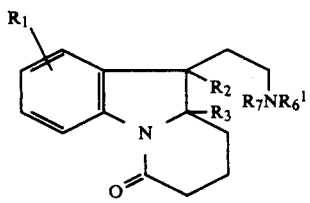
(IId)

wherein $R_6^1$ is as defined in formula (II) and the remaining variables are as defined in formula (I).

Suitable and preferred values for $R_6^1$ and $R_7$ are as described under formulae (II) and (IIa).

Another subgroup of compounds within formula (I) is of formula (III):

(III)

wherein $R_1$, $R_2$, $R_3$, $R_4$, $R_5$, and $R_7$ are as defined in formula (I) and $R_6^4$ is $NR_8^2 R_9^2 C_{1-7}$ alkyl where $R_8^2$ and $R_9^2$ are independently hydrogen or $C_{1-4}$ alkyl.

Suitable and preferred values for the variables are as described under formula (I).

Preferably $R_1$ is hydrogen.
Preferably $R_2$ and $R_3$ represent a bond.
Preferably $R_4$ and $R_5$ are both hydrogen.
Preferably $R_6^4$ is $-(CH_2)_5 NR_8^2 R_9^2$ where $R_8^2$ and $R_9^2$ are as defined.
Preferably $R_7$ is hydrogen.

Where compounds of formula (I) can exist in more than one stereoisomeric form, the invention extends to each of these forms and to mixtures thereof.

The invention further provides a process for the preparation of a compound of formula (I), or a pharmaceutically acceptable salt thereof, which process comprises the conversion of a compound of formula (V):

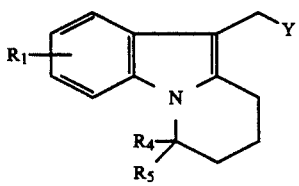

(V)

wherein $R_1$, $R_4$ and $R_5$ are as defined in formula (I) and Y is a group convertible to $CH_2NR_6'R_7'$ where $R_6'$ is $R_6$ as defined in formula (I) or a group convertible thereto and $R_7'$ is an amino protecting group or $R_7$ as defined in formula (I), into a compound of formula (Va):

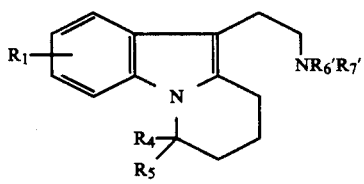

(Va)

and thereafter, optionally and as necessary, converting $R_6'$ when other than $R_6$ into $R_6$, removing any $R_7'$ amino protecting group, interconverting $R_6$ and/or $R_7$ to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Y may be conventional amine precursor. Suitable examples include CN, COQ where Q is H or a leaving group such as halo, $C_{1-4}$ alkoxy or carboxylic acyloxy, and $CH_2L$ where L is $CON_3$, $N_3$, $NO_2$ or X where X is a leaving group such as hydroxy, halo, $C_{1-4}$ alkoxy, $C_{1-4}$ alkanoyloxy, $C_{1-4}$ alkoxycarbonyloxy, tosyloxy or mesyloxy.

The reaction converting the compound of formula (V) into that of formula (Va) may be carried out under the conventional conditions appropriate to the particular group Y in formula (V).

Thus, when Y is $CH_2CON_3$, the conversion is a Curtius degradation carried out conventionally, by heating in dry inert solvent, such as benzene, and then subsequent hydrolysis of the thus formed isocyanate under acid conditions.

When Y is CN, the conversion is a reduction to the primary amine, for example with a reducing agent such as diborane or $LiAlH_4$ at elevated temperature and in an inert solvent such as tetrahydrofuran, or with hydrogen over Raney nickel in the presence of ammonia at ambient temperature in a polar solvent such as methanol.

When Y is CHO, the conversion is a condensation with hydroxylamine followed by reduction of the thus formed oxime over a metallic catalyst, or is a reductive amination with a primary or secondary amine using a reducing agent such as $NaBH_3CN$ in a polar solvent such as $CH_2Cl_2/CH_3OH$ at elevated temperature.

Alternatively the intermediate imine may be prepared in a non polar solvent such as benzene in the presence of an acid catalyst e.g. p-toluenesulphonic acid and reduced with a reducing agent such as $NaBH_4$.

When Y is COQ where Q is a leaving group, the conversion is a nucleophilic substitution by ammonia or a primary or secondary amine under conventional conditions appropriate for leaving group Q, followed by reduction of the resulting amide with e.g. $LiAlH_4$ in an inert solvent such as tetrahydrofuran at elevated temperature followed by work up. For example, when Q is halo such as chloro, the nucleophilic substitution may be carried out at ambient or lower temperature in the presence of an acid acceptor such as triethylamine in a polar solvent such as $CH_2Cl_2$, followed by work up to give the amide which may be reduced as just described.

When Y is $CH_2N_3$, the conversion is a reduction of the azide to the primary amine with e.g. hydrogen over a metallic catalyst.

When Y is $CH_2NO_2$, the conversion is a reduction of the nitro group to the primary amine with a reducing agent such as $LiAlH_4$, or hydrogen over Raney nickel or Pd/C catalyst in a polar solvent such as ethanol.

When Y is $CH_2X$, the conversion is a nucleophilic substitution by ammonia or a primary or secondary amine or azide ion, under conventional conditions appropriate for the leaving group X. Thus, when X is hydroxy, it is first converted into a good leaving group such as mesylate or tosylate (using mesyl or tosyl chloride respectively) or chloride (using $SOCl_3$). The nucleophilic substitution may be carried out at elevated temperature in a polar solvent such as acetonitrile in the presence of an acid acceptor such as diisopropyl ethylamine. Alternatively, the leaving group may be substituted by nitrile to yield a compound of formula (V) where Y=$CH_2CN$. Hydrolysis and conversion by conventional methods yields a compound where Y=$CH_2CON_3$ via the acid as described hereinafter.

Suitable examples of $R_6'$ convertible to $R_6$ include hydrogen or an amino protecting group.

In the resulting compound of formula (Va) in the case where $R_6'$ or $R_7'$ is an amino protecting group such as $C_{1-6}$ alkoxy carbonyl, aryloxycarbonyl, $C_{1-6}$ alkanoyl or phenyl $C_{1-7}$ alkanoyl, the protecting group may be removed by conventional procedures.

The conversion of any $R_6'$ amino protecting group to $R_6$ via the $R_6'$ hydrogen intermediate, the conversion of $R_6'$ hydrogen to $R_6$, or the interconversion of an $R_7$ hydrogen atom may be carried out by conventional amine alkylation such as simple alkylation or, more preferably, by acylation followed by reduction of the amide, or by reductive alkylation.

Acylation may be carried out using the appropriate acyl chloride or anhydride and the subsequent reduction of the resulting amide with $LiAlH_4$ in the presence of $AlCl_3$.

The reductive alkylation procedure is preferably carried out by heating with the aldehyde or ketone in an organic acid, such as acetic acid, then reducing the product in situ using an alkaline borohydride such as sodium borohydride or cyanoborohydride. The reaction can also be carried out in an alcohol, in which case the reduction can be carried out either chemically, for example with a borane such as trimethylammoniumborane or an alkaline borohydride or with hydrogen in the presence of a catalyst such as Raney nickel.

It is also possible to use an aprotic solvent, for example an aromatic solvent such as benzene or toluene, the water formed being eliminated either at room temperature by means of a drying-agent or under reflux heating of the solvent by means of a Dean-Stark water-separator; the reduction can then be expediently carried out with hydrogen in the presence of a catalyst such as palladiated carbon or platinum oxide. These methods may be subject to certain limitations, depending on the nature of the aldehyde or ketone used.

It is also possible to use a more universal method. For example, the $R_6'/R_7$ hydrogen compound and the aldehyde or ketone to be condensed are dissolved in a mixture of solvents which can advantageously be a methanol-dichloromethane mixture in the presence of a complex reducing agent such as quaternary ammonium cyanoborohydride or, more simply, an alkaline cyanoborohydride solubilised by a phase-transfer agent, for example sodium cyanoborohydride and aliquat 336 (Cf. Hutchins, R. O. and Markowitz, M., Journal of Organic Chemistry 1981, 46, pp. 3571-3574).

The alkylation, acylation or reductive alkylation may introduce the required moiety $NR_8R_9$ in the alkyl substituted $R_6$ directly, or alternatively by way of an amine precursor $Y^1$ which is convertible to $CH_2 NR_8' R_9'$ (where $R_8'$ and $R_9'$ are $R_8$ and $R_9$ or groups convertible thereto) analogously to the conversion of the group Y in the compound of formula (V). For example, the amine precursor $Y^1$ may be of the formula $CH_2X^1$ where $X^1$ is a leaving group as defined for X above, such as halo e.g. chloro which can be subsequently displaced by a compound $HNR_8R_9$. Where the alkylation reaction is of the acylation/reduction type, reduction of the amide described above may be carried out before or after this displacement.

Accordingly, the invention further provides a process for the preparation of a compound of the formula (I) or a pharmaceutically acceptable salt thereof which process comprises the conversion of a compound of the formula (Vb):

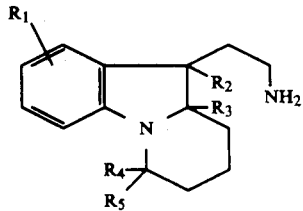

(Vb)

to a compound of formula (Vc):

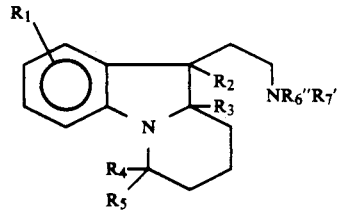

(Vc)

in which $R_6$ " is $C_{1-6}$ alkyl substituted by a group $Y^1$ where $Y^1$ is a group convertible to $CH_2NR_8' R_9'$ or $C_{1-6}$ alkanoyl substituted by $CH_2NR_8 R_9$ or $Y^1$ as defined, where $R_8'$ and $R_9'$ are $R_8$ and $R_9$ or groups convertible thereto, and $R_1$, $R_2$, $R_3$, $R_4$ and $R_5$ are as defined in formula (I), the conversion being followed by, or simultaneously with, optionally or as necessary, the reduction of $R_6''$ alkanoyl to $R_6''$ alkyl, the conversion of $Y^1$ to $CH_2NR_8'R_9'$, the conversion of $R_8'$ and $R_9'$ to $R_8$ and $R_9$, the reduction of the $R_4/R_5$ oxo group, the reduction of the $R_2/R_3$ double bond, and/or the formation of a pharmaceutically acceptable salt.

The conversion may be carried out as described above for the conversion of an $R_6'$, or interconversion of an $R_7$, hydrogen atom.

The invention provides intermediates of the formula (Vc).

The invention also provides intermediates of the formula (Vd):

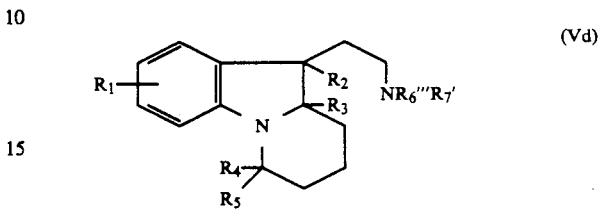

(Vd)

wherein $R_6'''$ is $C_{1-7}$ alkanoyl substituted by $NR_8R_9$ as defined in formula (I) and the remaining variables are as defined in formula (I).

Suitable and preferred values for the variables in formulae (Vc) and (Vd) are as described for the corresponding variables under formula (I).

The reduction of the $R_2/R_3$ bond may be carried out conventionally by the use of an alkaline borohydride in a polar aprotic solvent such as dimethylsulphoxide or by nitromethane in the presence of a strong organic acid such as methanesulphonic acid or in pure trifluoroacetic acid. Alternatively the bond may be reduced catalytically with hydrogen over platinum oxide catalyst in a solvent permitting protonation of the indolic nitrogen, such as ethanol containing fluoroboric acid or acetic acid containing trifluoroacetic acid.

When $R_4$ and $R_5$ together form an oxo group, compounds wherein $R_4$ and $R_5$ are both hydrogen may be prepared by reduction of the $R_4/R_5$ oxo group in formula (I) using a mixed hydride complexed with a Lewis acid, for example, the complex lithium aluminium hydride-aluminium chloride in an inert solvent such as diethyl ether. When an $R_6$ or $R_7$ group other than hydrogen is introduced initially by acylation to give the amide, simultaneous reduction of the $R_4/R_5$ oxo group and the amide moiety may be effected by appropriate choice of reducing agent, for example the mixed hydride complexed with a Lewis acid just described.

When $R_2$ and $R_3$ together form a bond and $R_4$ and $R_5$ together form an oxo group, simultaneous reduction of the double bond and the oxo group may be effected by the use of an alkaline borohydride as described above for the reduction of an $R_2/R_3$ bond.

It will be appreciated that these conversions may take place in any desired or necessary order.

Pharmaceutically acceptable salts of the compounds of formula (I) may be formed conventionally by reaction with the appropriate acid such as described above under formula (I).

Compounds of formula (V) in which Y is $CH_2CON_3$ may be prepared by the formation of the acid chloride followed by reaction of azide ion on an acid of formula (VI):

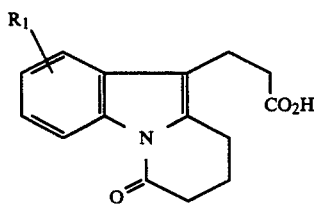

(VI)

This method is described in J. Am. Chem. Soc. 1981, 103, 6990-6992.

Acids of formula (VI) are known or may be prepared by conventional methods. For example, a phenylhydrazine is condensed with 4-oxoazelaic acid (ref. Von Pechmann et. al. Berichte 1904, 37, p 3816). The hydrazone thus obtained is subjected to a Fischer cyclisation to give the acid of formula (VI).

Compounds of formula (V) in which $R_4$ and $R_5$ are both hydrogen may be prepared by the reaction of a compound of formula (VII):

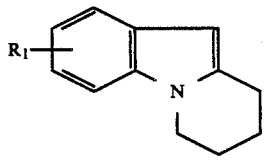

(VII)

with (i) ClCOCOR$_{11}$, where $R_{11}$ is alkoxy such as ethoxy or halo such as chloro, followed by reduction with LiAlH$_4$ to give a compound of formula (V) where Y is —CH$_2$OH which may subsequently be reacted with azide ion to give the corresponding compound where Y is —CH$_2$N$_3$;

(ii) CH$_2$=CH—R$_{12}$, where $R_{12}$ is a 1-carbonyl containing group or cyano, under basic conditions, followed by hydrolysis and reaction on the resulting acid group by azide ion as described above, to give a compound of formula (V) where Y is —CH$_2$CON$_3$;

(iii) formaldehyde in the presence of dimethylamine followed by reaction of cyanide ion on the resulting tertiary amine, if necessary after quaternization, to give a compound of formula (V) where Y is —CN;

(iv) CH$_2$=CHNO$_2$ under basic conditions to give a compound of formula (V) where Y is CH$_2$NO$_2$.

Compounds of formula (VII) can be prepared according to Hans Zimmer, J. Heterocylic Chemistry 21, 623(1984).

Compounds of formula (V) in which Y is CHO may be prepared from the corresponding compound in which Y is CN by a variety conventional procedures such as, for example, reaction with diisobutylaluminium hydride.

Compounds of formula (V) in which Y is COQ where Q is a leaving group may be prepared from the corresponding compound in which Y is CN by, for example, hydrolysis under acid conditions of the nitrile to give the corresponding acid, followed by conversion of the hydroxyl group to a leaving group Q such as chloro with a chlorinating agent such as oxalyl chloride. Interconversion of leaving groups Q may be carried out conventionally.

Compounds of formula (V) in which $R_4$ and $R_5$ are both hydrogen and Y is —CH$_2$CN, may alternatively be prepared by homologation of a compound of formula (VIII):

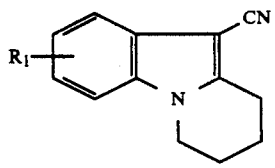

(VIII)

prepared according to D. N. Reinhoudt et al., Tetrahedron Letters 26 (5) 1985, 685-8. The nitrile is first reduced to the amine which is quaternised and reacted with cyanide ion to give the relevant compound of formula (V).

In the formulae (VI), (VII) and (VIII) above, $R_1$ is as defined in formula (I).

The invention further provides a pharmaceutical composition comprising a compound of formula (I), including pharmaceutically acceptable salts thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment of cerebrovascular disorders and/or disorders associated with cerebral senility in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.1 to 100 mg/kg; and such therapy may extend for a number of weeks or months.

At the above indicated dosage range, no adverse toxicological effects are indicated for the compounds of the invention.

In a further aspect the invention provides a compound of formula (I) for use as an active therapeutic substance.

The invention further provides a compound of formula (I), including pharmaceutically acceptable salts thereof, for use in the treatment of cerebrovascular disorders and/or disorders associated with cerebral senility.

The following examples illustrate the invention and the following descriptions illustrate the preparation of intermediates thereto.

Description 1

6-Oxo-6,7,8,9-tetrahydropyrido[1,2-a]indole-10-propionic acid. (D1)

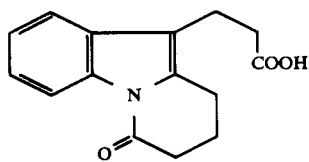

This compound has been described by Y. Ban in J. Amer. Chem. Soc. 1981, 103 (23), pp.6990–6992. Melting-point 163°–165° C. IR (KBr)$\nu$=3200–2500; 1700; 755 cm$^{-1}$.

Description 2

6-Oxo-10-(2-aminoethyl)-6,7,8,9-tetrahydropyrido[1,2-a]indole hydrochloride (D2)

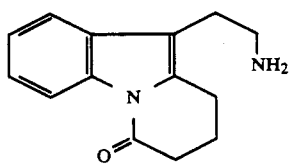

(a) Acid chloride: 1.5 g oxalyl chloride (11.5 mmoles) and 1 drop of DMF were added dropwise to a suspension of 1.5 g (5 mmoles) of the acid of Description 1 in 4 ml benzene. When the liberation of vapours slowed down the mixture was heated for 30 minutes at 60°–70° C. The brown solution thus obtained was concentrated to dryness in vacuo, leaving a residue of maroon-coloured crystals, which were used as they were for stage b).

(b) Acyl azide: The crude acid chloride from stage (a) was dissolved in 12 ml dry acetone and added dropwise to an ice-cooled solution of 0.4 g sodium azide in 1 ml water and stirred for a further 30 minutes at 0° C., then for 30 minutes at room temperature. The mixture was then diluted with 25 ml water, the precipitate formed was filtered off, washed with water and then dried in vacuo at room temperature, giving the corresponding acyl azide as a white crystalline solid.

(c) 56.3 mmoles crude azide from stage (b) was dissolved in 70 ml drybenzene and heated under reflux for 40 minutes. There was a substantial liberation of nitrogen and the solution turned black. 100 ml benzene and 24 ml concentrated HCl were then added and heated under reflux for 1 hour.

There was a substantial liberation of gas/vapours, and then a precipitate was formed. The solution was then concentrated to dryness, giving the crude amine hydrochloride. Recrystallisation in a 4/1 mixture of ethanol/water produced a white crystalline solid D2 described by Y. Ban(ref.cited) of m. pt. 330°–335° C. (decomposition). IR (KBr)$\nu$=3200–2400; 1700; 745 cm$^{-1}$. UV (ethanol)$\lambda$max=243; 267; 292; 302 nm.

Description 3

6-Oxo-10-(2-(5-chlorovaleryl)aminoethyl)-6,7,8,9-tetrahydropyrido[1,2-a]indole (D3)

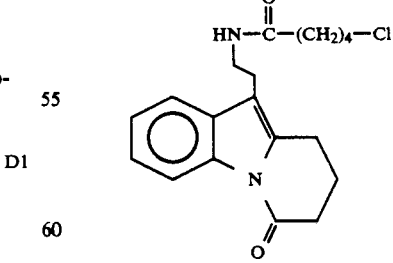

A solution of 15 g 5-chlorovaleric acid chloride in 100 ml CHCl$_3$ was added to an ice-cooled solution of 25 g D2 and 30 g triethylamine in 300 ml dry CHCl$_3$ After addition of the acid chloride the mixture was left to stand for 2 hours at room temperature, then twice shaken with a 10 percent solution of citric acid and once with brine. After drying and evaporation the residue was crystallized from ethyl acetate. 24 g amide D3 were obtained, m.pt 98° C.

Description 4

6-Oxo-10-(2-(5-(3,5-dimethyl piperidyl-(1))valeryl)aminoethyl)-6,7,8,9-tetrahydropyrido[1,2-a]indole (D4)

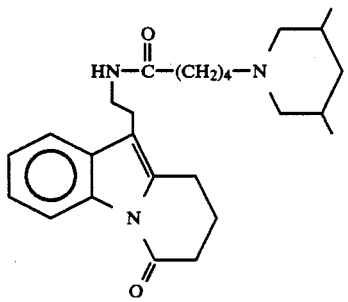

17.4 g D3 and 1.7 g 3,5-dimethylpiperidine were heated in 100 ml DMF at 60° C. for 16 hours.

After addition of 500 ml water and extraction with ethyl acetate the organic phase was dried and evaporated. the residue was crystallised from di-isopropylether to give D4. Yield: 14.7 g. M.pt: 135°-6° C.

Description 5

10-(2-Aminoethyl)-6,7,8,9-tetrahydropyrido[1,2-a]indole hydrochloride (D5)

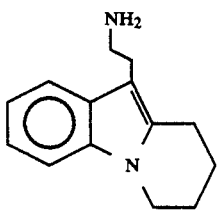

Compound D5 is described in EP-O 167901-A as Example 19 on page 45.

Description 6

10-(2-(5-Chlorovaleryl)aminoethyl)-6,7,8,9-tetrahydropyrido [1,2-a]indole (D6)

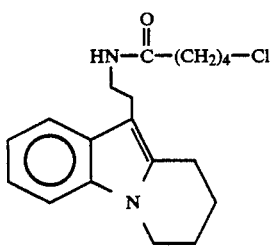

43 g (0.2 mole) Amine D5 were dissolved in 300 ml CHCl$_3$ and 0.5 mole triethylamine. A solution of 0.3 mol 5-chlorovaleric acid chloride was added at 0°-5° C. and the solution left to stand for 4 hours at room temperature, then twice shaken with a 10 percent solution of citric acid and sodium carbonate, respectively. After drying and evaporation, the residue was crystallised from ethyl acetate to yield 56 g D6.

Mpt: 93° C.

Description 7

10-(2-(5-(3,5-Dimethyl-piperidyl-(1))valeryl)aminoethyl)-6,7,8,9-tetrahydropyrido[1,2-a]indole (D7)

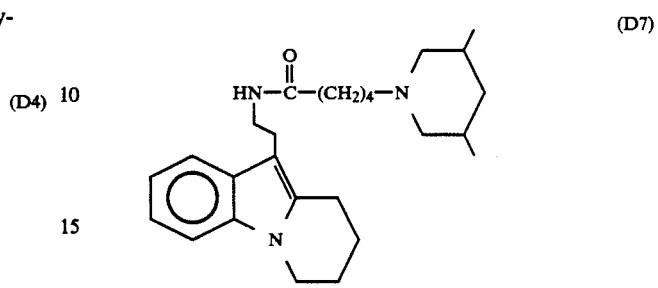

8 g D6, 5.7 g 3,5-dimethylpiperidine, 5.1 g diisopropylethylamine and 1.5 g KI in 100 ml DMF were heated at 80° C. for 20 hours. After dilution with 500 ml water and extraction with ethyl acetate the organic phase was extracted 3 times with 100 ml 1N HCl solution, the aqueous phase made alkaline with sodium hydroxide solution and extracted with ether. The ether solution was dried, evaporated and the residue crystallized from diisopropyl ether to yield 4.4 g D7.

Mpt: 123° C.

NMR (CDCl$_3$) δ=6.9–7.6 [4] m; 5.8 [1] tr broad (exchange); 4.0 [2] tr J=6Hz; 3.5 [2] q (after exchange tr); 0.8 [6] tr J=6 Hz.

Description 8 to 10

The following compounds were prepared analogously:

10-(2-(5-Dimethylaminovaleryl)aminoethyl)-6,7,8,9-tetrahydropyrido [1,2-a]indole (D8)

10-(2-(5-(Pyrrolidinyl-(1))valeryl)aminoethyl)-6,7,8,9-tetrahydropyrido [1,2-a]indole (D9)

10-(2-(5-(Morpholinyl-(1))valeryl)aminoethyl)-6,7,8,9-tetrahydropyrido [1,2-a] indole (D10)

10-(2-(5-(Piperidyl-(1))valeryl)aminoethyl)-6,7,8,9-tetrahydropyrido [1,2-a]indole (D11)

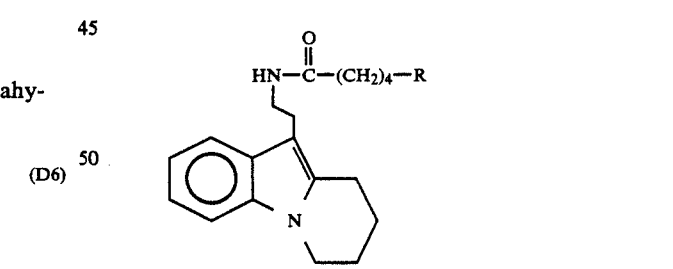

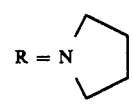

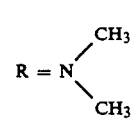

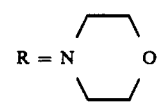

-continued

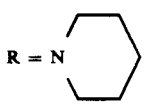
(D11)

Compounds D8 and D10 were obtained as yellow oils and used in the following examples without further purification.

Compound D9:
Mpt: 81° C.
NMR (CDCl3):δ=7.0–7.7 [4] m; 5.75[1] s broad (exchange); 4.0 [2] tr J=6 Hz; 3.48 [2] q J=6 Hz (after exchange tr J=6 Hz); 3.9 [4] tr.

Compound D11:
Mpt: 183°–184° C. (hydrochloride).
NMR (DMSO d6):δ=10.62 [1] s (exchange); 8.02 [1] tr. J=5.4 Hz; 7.6–6.95 [4] m; 4.02 [2] tr. J=5.7 Hz; 3.55–2.65 [12] m; 2.3–1.25 [16]m.

EXAMPLE 1

10-(2-(5-(3,5-Dimethylpiperidyl-(1))pentyl)aminoethyl)-6,7,8,9-tetrahydropyrido[1,2-a]indole (E1)

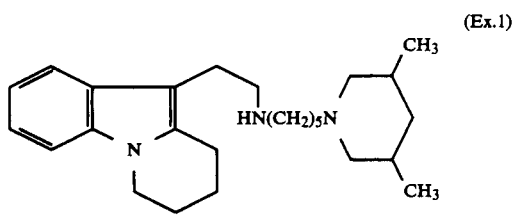
(Ex.1)

Method A:
5 g D4 was reduced with a mixture of 2.3 g LiAlH4 and 6.7 g AlCl3 in 250 ml ether and 250 ml THF. After working up, the base was crystallised by the addition of an ethanolic solution of fumaric acid. 2.4 g Fumarate of E1 were obtained.
Mpt: 110°–111° C.
NMR (DMSO d6) δ=0.85 [6]d J=6 Hz; 4[2] tr J=7 Hz; 5.5–6.4[2.5] exch.; 6.6[3]s; 6.9–7.6[4]m.

Method B:
4.4 g D7 were dissolved in 50 ml THF and dropped into a boiling suspension of 3 g LiAlH4 in 50 ml THF. After 3.5 h of reflux the excess of LiAlH4 was destroyed by addition of water, the precipitate was filtered off, washed with CH2Cl2 and the filtrate evaporated. The residue was chromatographed on SiO2 and the pure polar isomer of E1 (seems to be trans dimethyl) was isolated as the dihydrochloride by addition of ethanol/HCl.
Mpt: 231° C.

|  | C | H | N | Cl |
|---|---|---|---|---|
| (½H2O) calc. | 65.39 | 9.18 | 8.79 | 14.84 |
| found: | 65.49 | 9.18 | 8.63 | 14.45 |

NMR (DMSO d6) δ=10.8 [1] s broad (exchange); 9.3 [2]s broad (exchange); 6.9–7.7 [4] m; 4.0 [2] tr J=6 Hz; 0.88 [6] d

EXAMPLE 2

10-(2-(5-Dimethylaminopentyl)aminoethyl)-6,7,8,9-tetrahydropyrido [1, 2-a]indole (E2)

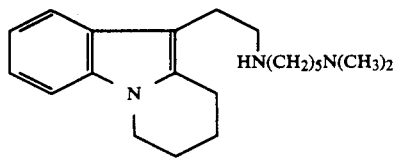
(Ex.2)

10 g D8 oil was dissolved in 50 ml THF, added to a suspension of 3 g LiAlH4 in 100 ml THF and refluxed for 25 h. Work up as described for E1 Method B. The product was isolated as the dihydrochloride.
Mpt: 250° C.

|  | C | H | N | Cl |
|---|---|---|---|---|
| calc. | 62.99 | 8.81 | 10.49 | 17.71 |
| found: | 62.61 | 8.68 | 10.55 | 16.98 |

NMR (DMSO d6) δ=11 [1] s broad (exchange); 9.6 [2]s broad (exchange); 6.9–7.7 [4] m; 4 [2] tr J=6 Hz; 2.7 [6] s

EXAMPLE 3

10-(2-(5-(Piperidyl-(1))pentyl)aminoetyl)-6,7,8,9-tetrahydropyrido [1,2-a]indole (E3)

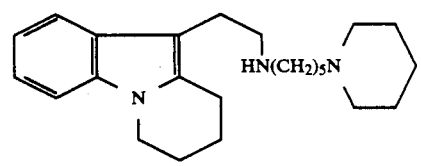
(Ex.3)

Compound E3 was prepared analogously to compound E2, from 3.5 g D11 using 2 g LiAlH4 and a 12 h reflux.
Mpt: 238° C. (dihydrochloride)
NMR (DMSO d6): δ=10.6 [1] s (exchange); 9.35 [2] s (exchange); 7.67–6.9 [4] m; 4.0 [2] tr. J=5.5 Hz; 3.6–2.6 [14] m; 2.2–1.2 [16] m.

EXAMPLE 4

10-(2-(5-(Pyrrolidyl-(1))pentyl)aminoethyl)-6,7,8,9-tetrahydropyrido [1,2-a]indole (E4)

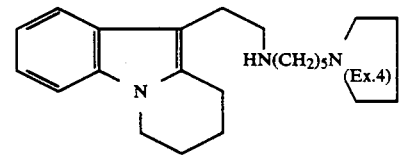
(Ex.4)

Compound E4 was prepared analogously to compound E2, from 6.5 g D9 using 3 g LiAlH4 and a 4 h reflux
Mpt: (dihydrochloride) 255°–6° C.

|  | C | H | N | Cl |
|---|---|---|---|---|
| (½H2O) calc. | 63.44 | 8.70 | 9.65 | 16.28 |
| found: | 63.17 | 8.64 | 9.62 | 16.09 |

NMR (DMSO d6) δ=9.85 [3] s broad (exchange); 6.9-7.3 [3] m; 7.7 [1] m; 4 [2] tr J=6 Hz.

EXAMPLE 5

10-(2-(5-(Morpholinyl-(1))pentyl)aminoethyl-6,7,8,9-tetrahydropyrido [1,2-a]indole (E5)

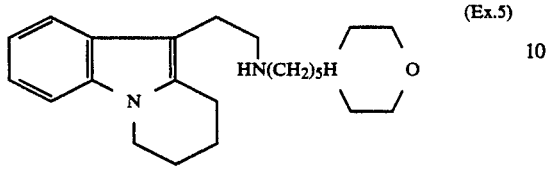
(Ex.5)

Compound E5 was prepared analgously to compound E2, from 9.7 g D10 oil using 4 g LiAlH4 and a 2 h reflux. Mpt: 252°-3° C.

|  | C | H |
|---|---|---|
| (½H2O) calc. | 61.19 | 8.48 |
| found: | 60.83 | 8.43 |

NMR (DMSO d6) δ=11.4 [1] s broad (exchange); 9.3 [2] s broad (exchange); 7.0-7.7 [4] m; 3.7-4.2 [6] m; 1.2-2.3 [10] m.

Pharmacological Data

Triethyltin-induced cerebral oedema in the rat.

The cerebral oedema is induced by oral administrations repeated for 5 consecutive days—one administration per day—of triethyltin chloride at a dose of 2 mg/kg. The study substances are also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used for each compound studied:

1 control group
1 group intoxicated with triethyltin
1 group intoxicated with triethyltin and treated with the studied compound.

The rats are killed on the evening of the fifth day; the brain is removed, weighed fresh and after desiccation to constant weight and the water content of each brain is calculated:

[H2O]=fresh weight—dry weight.

The following are then calculated:
the mean water content (M±Sm%) of each group;
the protection index P due to the administered compound:

$$P\% = 1 - \frac{[H_2O] \text{ treated group} - [H_2O] \text{ control group}}{[H_2O] \text{ triethyltin group} - [H_2O] \text{ control group}} \times 100$$

The results are given in Table 1.

TABLE 1

| COMPOUND | n | DOSAGE | EFFECT (P) % reduction | SIGNIFICANCE* |
|---|---|---|---|---|
| E1 (Method A) | 6 | 2 × 50.0 | 65 | 0.01 |
| E2 | 6 | 2 × 12.5 | 59 | 0.01 |

*unpaired Wilcoxon signed rank test
n = number of animals.

Toxicity
No toxic effects were observed in the above tests.

We claim:
1. A compound of formula (I) or a pharmaceutially acceptable salt thereof:

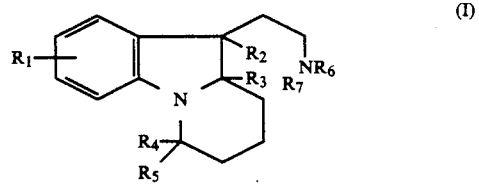
(I)

wherein:
R1 is hydrogen, C1-6 alkyl, C1-6 alkoxy or halogen;
R2 and R3 are both hydrogen or together represent a bond;
R4 is hydrogen and R5 is hydrogen or R4 and R5 together represent an oxo group;
R6 is C1-7 alkyl substituted by NR8R9 where R8 and R9 are independently hydrogen or C1-4 alkyl; and
R7 is hydrogen or C1-4 alkyl.

2. A compound according to claim 1 of formula (III):

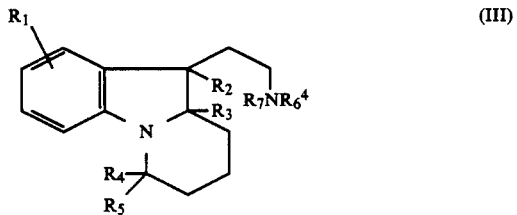
(III)

wherein R1, R2, R3, R4, R5, and R7 are as defined in claim 1 and R6⁴ is NR8² R9² C1-7 alkyl where R8² and R9² are independently hydrogen or C1-4 alkyl.

3. A compound according to claim 2 wherein R6 is —(CH2)5NR8²R9² in which R8² are as defined in claim 2.

4. A compound according to claim 1 wherein R1 is hydrogen.

5. A compound according to claim 1 wherein R2 and R3 together represent a bond.

6. A compound according to claim 1 wherein R4 and R5 are both hydrogen.

7. A compound according to claim 1 wherein R7 is hydrogen.

8. 10-(2-(5-Dimethylaminopentyl)aminoethyl)-6, 7, 8, 9-tetrahydropyrido [1, 2-a]indole or a pharmaceutically acceptable salt thereof.

9. A pharmaceutical composition for the treatment of cerebrovascular disorders and/or disorders associated with cerebral senility comprising an effective amount of a compound according to claim 1 and a pharmaceutically acceptable carrier.

10. A method of treatment of cerebrovascular disorders and/or disorders associated with cerebral senility in mammals, which comprises administering to the sufferer an effective amount of a compound according to claim 1.

* * * * *